United States Patent [19]

Simpson et al.

[11] Patent Number: 5,489,511
[45] Date of Patent: Feb. 6, 1996

[54] SPECIFIC AND SENSITIVE DIAGNOSTIC TEST FOR LYME DISEASE

[75] Inventors: Warren J. Simpson; Tom Schwan; Claude Garon, all of Hamilton, Mont.

[73] Assignee: The United States of America as represented by the Department of Health and Human Services, Washington, D.C.

[21] Appl. No.: 173,718

[22] Filed: Dec. 27, 1993

Related U.S. Application Data

[63] Continuation of Ser. No. 898,233, Jun. 12, 1992, abandoned, which is a continuation of Ser. No. 427,735, Oct. 26, 1989, abandoned.

[51] Int. Cl.⁶ ............................. C12Q 1/68; C07H 21/02
[52] U.S. Cl. ............................. 435/6; 536/23.7; 536/24.3
[58] Field of Search ....................... 435/6, 810; 436/501, 436/808; 536/23.7; 935/78

[56] References Cited

PUBLICATIONS

Biosis No. 88075033, Schwan, T. G., et al., "Identification of *Borrelia burgdorferi* and *B. hermsii* Using DNA Hydridization Probes", *J. Clin. Microbiol.*, vol. 27(8), pp. 1734–1738 (1989).

Biosis No. 85089670, Barbour, A. G., "Plasmid Analysis of *Borrelia burgdorferi*, the Lyme Disease Agent", *J. Clin. Microbiol.*, vol. 26(3), pp. 475–478 (1988).

Biosis No. 83013443, Howe, T. R. et al., "Organization of Genes Encoding Two Outer Membrane Proteins of the Lyme Disease Agent *Borrelia brugdorferi* within a Single Transcriptional Unit", *Infect. Immun.*, vol. 54(1), pp. 207–212 (1986).

The New England Biolabs Catalogs. 1986, p. 60.

*Primary Examiner*—Margaret Parr
*Assistant Examiner*—Eggerton Campbell
*Attorney, Agent, or Firm*—Morgan & Finnegan

[57] ABSTRACT

A sensitive DNA probe for detecting infection by *Borrelia burgdorferi*, the causative agent of Lyme disease, is provided.

3 Claims, 8 Drawing Sheets

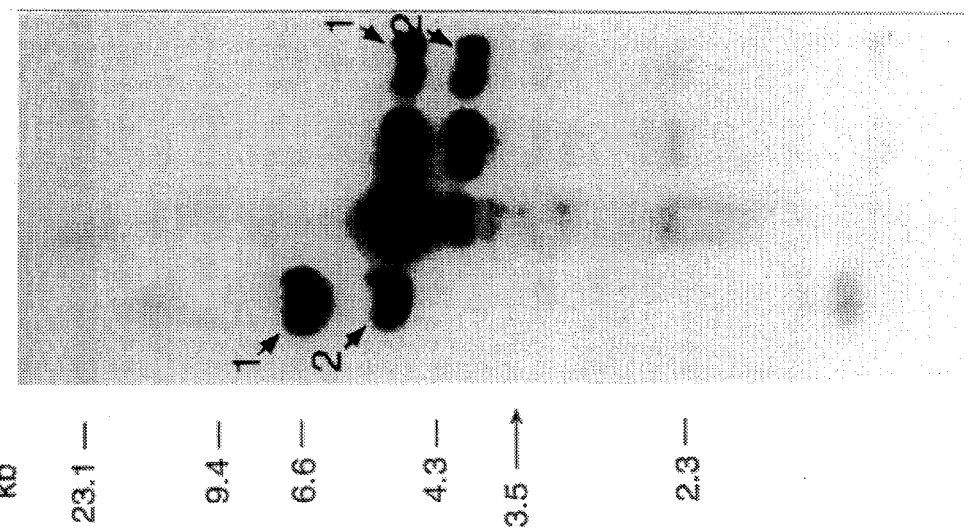
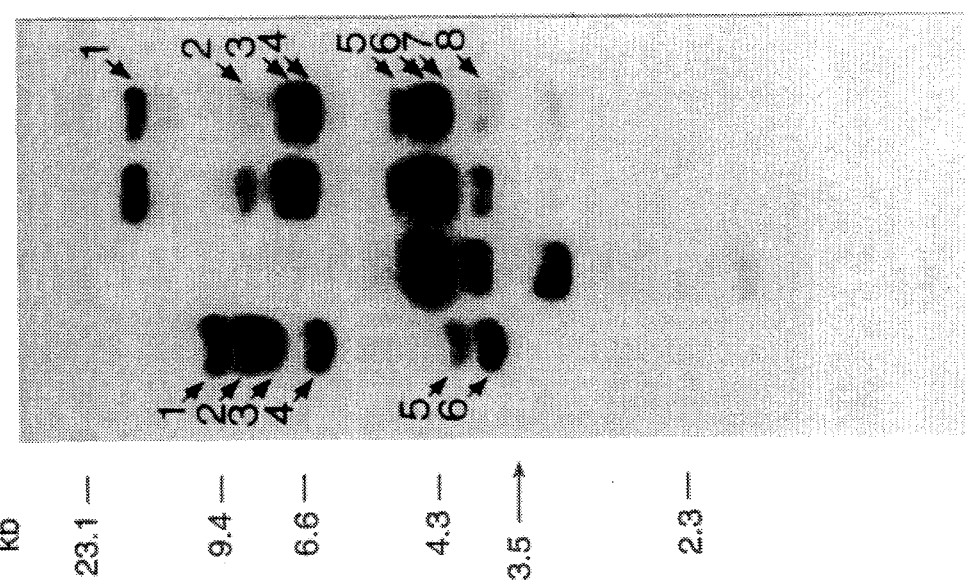
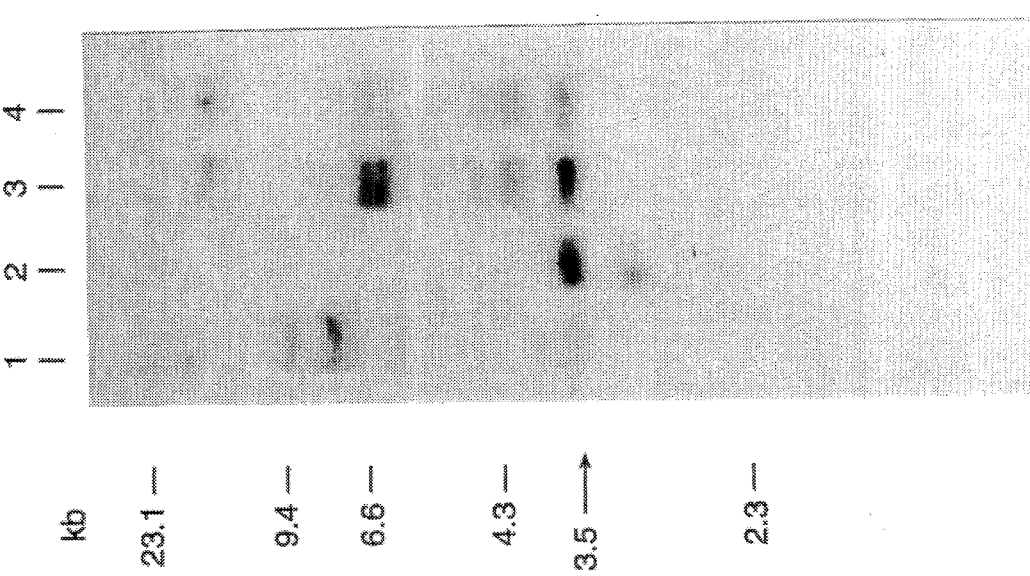

SPECIFIC AND SENSITIVE DIAGNOSTIC TEST FOR LYME DISEASE

This application is a continuation of U.S. application Ser. No. 07/898233, filed on Jun. 12, 1992, which is now abandoned, which is a continuation of U.S. application Ser. No. 07/427,735, filed in Oct. 26, 1989, which is now abandoned.

The present invention is related generally to diagnostic tests. More particularly, the present invention is related to providing specific and sensitive diagnostic probes for detecting infection by *Borrelia burgdorferi*, the causative agent of Lyme disease.

Lyme borreliosis, which is caused by *Borrelia burgdorferi*, is characterized by a wide range of clinical manifestations which may include severe neurological and arthritic complications. Officially recognized in North America in 1975, Lyme borreltosls is now the most prevalent tick-borne disease in the United States and has a worldwide distribution, including Europe where its spirochetal etiology eluded physicians since the early 1900's.

Because of the serious nature of this disease, a species-specific test for detecting the presence of the causative agent of this disease is desirable.

SUMMARY OF THE INVENTION

It is, therefore, an object of the present invention to provide diagnostic DNA probes for detecting the presence of *B. burgdorferi* in a biological sample.

Various other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 shows the results of an autoradiograph from the hybridization of $^{32}$P-radiolabelled insert DNA from pSPR14 (A), pSPR13 (B) and pSPR9 (C) with EcoRI digested total DNA from strain ECM-NY-87 (lane 1), purified SC plasmid DNA from strain Sh-2-82 (lane 3), and total DNA from strain Sh-2-82 (lane 4). Lane 2 contains EcoRI digested pSPR14 (A), pSPR13 (B), and pSPR9 (C). DNA fragments less than 3.5 kb in length resulted from degenerative EcoRI cleavage, as indicated by their presence in both the recombinant and spirochete DNA preparations, and were shown not to hybridize with pUC13 sequences (data not shown). Linear molecular weight markers are indicated in kb on the left. Arrows denote EcoRI fragments that hybridize with the respective probes.

DETAILED DESCRIPTION OF THE INVENTION

Figure 1A:
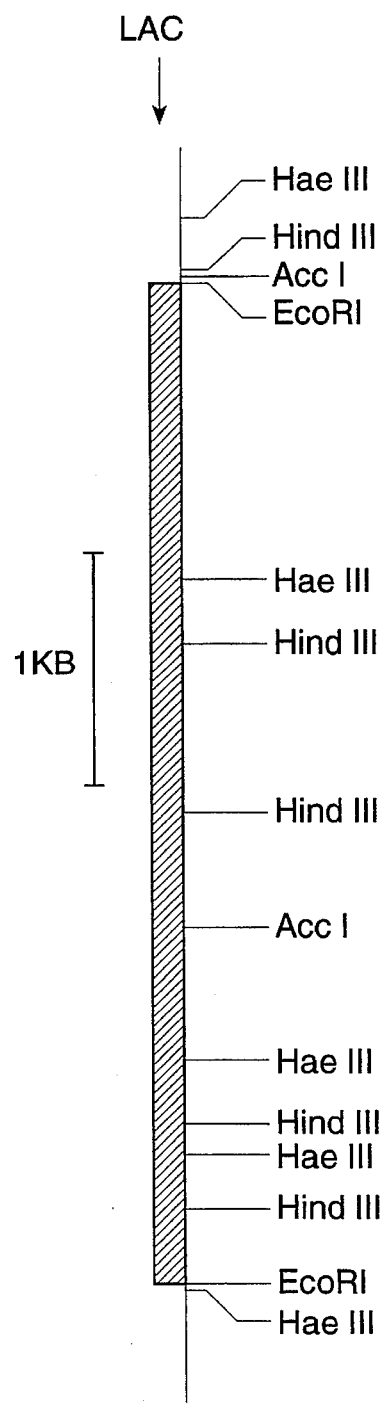
FIG. 1 shows the linear genetic map of pSPR9, pSPR13 and pSPR14. The striped block corresponds to spirochete DNA. There were no restriction sites within the three spirochete EcoRI fragments for the endonucleases AvaI, AvaII, SalI, KpnI and PvuII. The arrow indicates the orientation of the Lac promoter and the direction of transcription.

The above and various other objects and advantages of the present invention are achieved by DNA probes which hybridize specifically and selectively with DNA of supercoiled (SC) circular and certain linear plasmids of *B. burgdorferi*.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and limiting.

MATERIALS AND METHODS

Bacterial strains

*B. burgdorferi* strains Sh-2-82, ECM-NY-86 and B31 have been described previously (Schwan et al, 1988, *Infect. Immun.* 56:1831–1836). Strain CA-3-87 was isolated in 1987 from naturally infected *Ixodes pacificus* ticks from California. Strains CT26816, CT21343 and CT20004 were provided by Dr. John F. Anderson, Connecticut Agriculture Experimental Station, New Haven, Conn. Strain CT26816 was isolated from a naturally infected mole (genus *Microtus*) from Rhode Island in 1975; strain CT21343 was isolated from a naturally infected white-footed mouse (*P. leucopus*) from Wisconsin in 1986; strain CT20004 was isolated from naturally infected *I. ricinus* ticks from France in 1985. With the exception of strain B31, all isolates had not been passaged in culture more than five times since their original isolation and were shown to be infectious for *P. leucopus* or Syrian hamsters (*Mesocricetus auratus*) based on their isolation from experimentally infected animals after two weeks postinoculation (data not shown). The form of strain B31 used in this study was a highly passaged variant which has lost several SC and linear plasmids (Barbour, 1988, *J. Clin. Microbtol.* 26:475–478; Schwan et al, supra). *B. hermsii* strains FRG (FG) and BHC (HS1 serotype C) and strains representing *B. coriaceae* (Co53), *B. parkeri*, *B. turicatae* and *B. anserina* have been described previously (Schwan et al, 1989, *J. Clin. Microbiol.* 27: In press)

DNA purification.

Borrelial cells from which DNA was purified were cultured in BSK-II media at 32° C. Cultures were routinely checked by dark-field microscopy for contamination and the number of spirochetes. Total DNA, which included all plasmids and chromosomal DNA, was purified from a 500 ml stationary phase borreital culture by a modification of the previously described method (Barbour, 1988, *J. Clin. Microbiol.* 26:475–478). Cells were recovered by centrifugation, washed once in 20 ml of PBS plus 5 mM $MgCl_2$ and resuspended in 2.4 ml TES (50 mM Trts, pH 8.0; 50 mM EDTA; 15% [w/v] sucrose). Lysozyme (Sigma Chemical, Company, St. Louis, Mo.) was added to a final concentration of 1 mg/ml and the cell suspension was then placed on ice for 10 min. Cell lysis was achieved by adding 3 ml of TES plus 1% (v/v) sodium deoxycholate and gently mixing for 10 min at room temperature. 100 pl of proteinase K (10 mg/ml) (Sigma) was then added and the sample was incubated at 37° C. for 1 hr. After proteinase K treatment, the DNA was extracted twice with 1 volume of phenol-chloroform-tsoamyl alcohol (24:1, v/v) and once with chloroform-isoamyl alcohol (24:1, v/v). The DNA was ethanol precipitated, washed twice with 70% ethanol and resuspended to a final concentration of 1 mg/ml in TE (10 mM Tris, pH 7.6; 1 mM EDTA).

*B. burgdorferi* SC plasmid DNA was purified from total DNA by two consecutive cesium chloride-ethidtum bromide density-gradients (Plasterk et al, 1985, *Nature* (London) 318:257–263), employing 70,000 rpm for 4 hr at 18° C. in a Beckman VTi80 rotor. The SC plasmid pool, which was the denser of two bands visualized by long wave UV illumination, was precipitated once with ethanol after removal of the ethidium bromide and resuspended in a minimal volume of TE.

Linear plasmids were purified from the less dense band after a second gradient was performed to ensure that this preparation did not contain contaminating SC plasmids. Contaminating linear duplexes were removed by ion-exchange column chromatography according to the method described by Garon and Petersen (1986, *Gene Anal. Techn.* 4:5–8). Briefly, linear DNA was denatured in the presence of 0.2 M NaOH for 10 min. and then the pH was adjusted to 8.0. The salt concentration was adjusted to 0.5 M and the sample was immediately applied to a NAGS 37 mini column [Bethesda Research Laboratories, Gaithersburg, Md., (BRL)] equilibrated with 0.5 M NaCl. Linear plasmids were then eluted from the column with 0.8 M NACl, ethanol precipitated and resuspended in a minimal volume of TE.

Recombinant SC plasmids from *Escherichia coli* were extracted from 500 ml cultures and purified as previously described (Simpson et al, 1987, *Infect. Immun.* 55:2448–2455), except dye-buoyant density gradients were performed as above.

Cloning of repeated DNA and restriction enzyme digestion

SC plasmid-enriched DNA (1 µg) from *B. burgdorferi* strain Sh-2-82 was digested with EcoRI and the resulting fragments were cloned in *E. coli* strain DHSα (BRL) using dephosphorylated pUC13 (BRL). Ligation reactions were incubated at 16° C. for 12 hr with freshly prepared ligation buffer (50 mM Tris pH 7.6; 10 mM MgCl; 20 mM dithiothreitol; 1 mM ATP) and rubidium chloride-induced competent cells were transformed as previously described (Maniatis et al, 1982, Molecular cloning, a laboratory manual. Cold Spring Harbor Laboratory, Cold Spring Harbor, N.Y.) were done to identify clones that hybridized to pBBCl from strain Sh-2-82. This plasmid was recovered from agarose gels (Schwan et al, supra) and labelled with $[\alpha\text{-}^{32}P]dCTP$ by nick translation according to the directions of the manufacturer (nick translation kit, BRL). The probe was boiled for 4 min and then quenched on ice immediately before adding to hybridization buffer.

Restriction endonucleases were purchased from Boehringer Mannhelm Biochemicals (Indianapolis, Ind.), and digestions were performed as recommended by the manufacturer.

Agarose-gel electrophoresis and Southern analysis

Electrophoresis of undigested Borrelia DNA was in 0.4% agarose gels and restriction enzyme digested DNA was in 0.6% agarose gels at 12 V for 16 hr. The methods of transferring DNA from agarose gels to nitrocellulose, high-stringency hybridization (which permitted 10% basepair mismatch), and autoradiography have been described previously (Spanler et al, 1983, *Virology* 130:514–522), except that the prehybridization and hybridization buffers and temperatures were as described by Schwan et al (supra).

The DNA probes representing pSPR9, pSPR13 and pSPR14 from their EcoRI inserts were recovered from agarose gels using GeneClean (BIO 101 Inc., LaJolla, Calif.) and radiolabelled as described above.

Heteroduplex mapping

Isolated DNA of plasmids pSPR13 and PSPR14 was digested with AvaII. Equal amounts (0.6 µg) were mixed, denatured with alkali and renatured for 30 min at 30° C. in a solution containing 50% formamide, 0.1 M Tris pH 8.0, 0.05 M NaCl, and 1 mM EDTA, Following the incubation period, samples were mounted for electron microscopy as previously described (Garon, 1986. Electron microscopy of nucletc acids, p 161–181. In H. C. Aldrich and W. J. Todd (ed), Ultrastructure techniques for microorganisms. Plenum Press, New York). Spreading mixtures contained either: a) 56% formamide, 0.08 M Trictne, 0.2 M NaCl and 0.008 M EDTA; or b) the same solution without sodium chloride was omitted. Hypophase solutions contained 0.01 M Tris pH 8.0 and 0.001 M EDTA. Grids were stained with uranyl formate and rotary shadowed with platinum-palladium as described (Garon, supra). Grids were examined in a JEOL 100 B electron microscope at 40 kv accelerating voltage. Electron micrographs were taken on Kodak Electron Image plates at a magnification of 7,000 X. The magnification was calibrated for each set of plates with a grating replica (E. F. Fullam Inc., Schenectady, N.Y.) and contour lengths measured with a Numonics Graphic Calculator interfaced to a Tektronics 4052 A computer. DNA molecules of known length were used as calibration standards.

RESULTS

Cloning of repeated DNA

By electron microscopy, *B. burgdorferi* strain Sh-2-82 was shown to carry six SC plasmids (data not shown), including a 8.4 kb circle which was originally thought to be .7.6 kb, that is readily lost during *in vitro* cultivation (Schwan et al, supra). In the course of cloning this plasmid, designated here as pBBC1, a pUC13 library was constructed in *Escherichia coli* with a SC plasmid-enriched fraction from strain Sh-2-82 digested with EcoRI. pBBC1 has a single EcoRI recognition sequence and therefore is linearized when digested with this enzyme. *E. coli* recombinants were probed for spirochete DNA fragments by colony hybridization with $^{32}$P-labelled pBBC1. Two clones that hybridized with pBBC1 were identified and shown to have inserts of 4.2 kb (pSPR13) and 3.5 kb (pSPR14) (FIG. 1). pSPR13 and pSPR14 hybridized with a 4.2 kb (band 6) and a 3.5 kb (band 8) EcoRI fragment from both total DNA and a SC plasmid-enriched fraction from the tick isolate, strain Sh-2-82 (FIG. 2A and 2B, lanes 3 and 4). This indicates that the cloned fragments are not deletion variants of the linearized form (8.4 kb) of pBBC1. Bands 6 and 8 correspond to the cloned EcoRI fragments carried by pSPR13 and pSPR14 respectively. Both clones hybridized with at least seven additional EcoRI fragments from the same set of DNAs obtained from strain Sh-2-82 (FIG. 2A and 2B, lanes 3 and 4), and both hybridized with six similar sized EcoRI fragments in total DNA from a second spirochete that was isolated from human skin, strain ECM-NY-86 (FIG. 2A and 2B, lane 1). These data indicate that pSPR13 and pSPR14 represent a class of closely related DNA sequences in *B. burgdorferi* that recur in several plasmids. These will be referred to as repeated DNA sequences.

Several clones derived from the pUC13 library that did not hybridize with pBBC1 were selected at random and examined for unrelated spirochete DNA sequences to see if the DNA library contained more than one type of repeated sequence. One additional clone was identified, pSPR9, which carried a 4.3 kb EcoRI insert (FIG. 1) that did not hybridize with either pSPR13 or pSPR14 (data not shown). pSPR9 hybridized with two distinct EcoRI fragments in both total DNA and SC plasmid-enriched preparations from strain Sh-2-82 (FIG. 2C, bands 1 and 2) and hybridized with several DNA fragments in total DNA from strain ECM-NY-86. pSPR9 did not hybridize with the EcoRI fragments that hybridized with pSPR13 and pSPR14. The lack of DNA sequence similarity between pSPR9 and pSPR13/pSPR14 indicates there are at least two types of repeated DNA sequences in *B. burgdorferi*. Since the same size fragments as those detected in total DNA from strain Sh-2-82 were found in the SC plasmid-enriched fraction from the same strain, it suggests that these repeated DNA sequences are restricted to SC plasmids in strain Sh-2-82.

Distribution and plasmid-specificity of repeated DNA

Figure 3A:
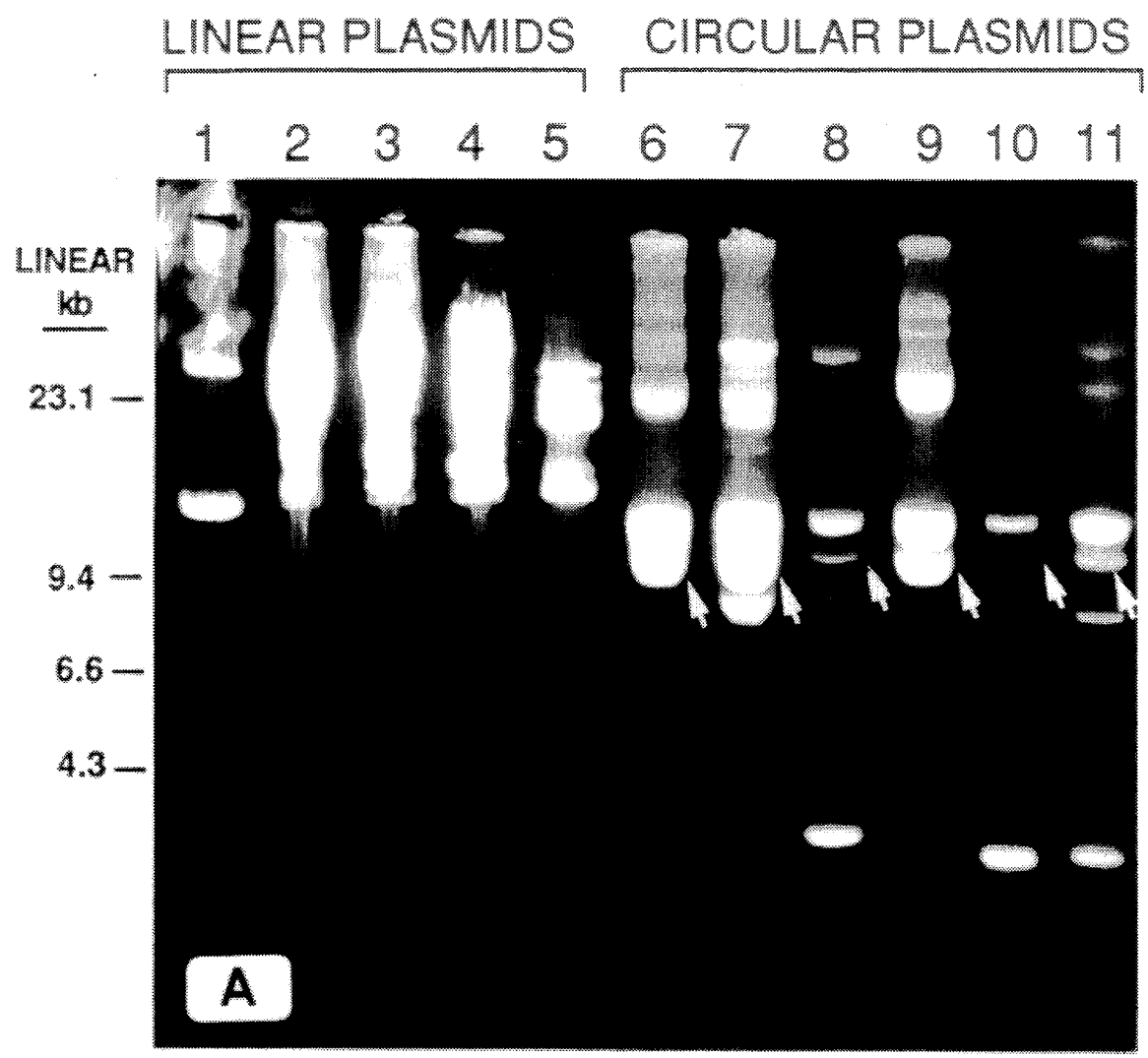
FIG. 3 shows the ethidtum bromide stained gel of purified linear and SC plasmids from unrelated *B. burgdorferi* isolates (A). Autoradiograph showing the same gel after blotting to nitrocellulose and hybridization with $^{32}$P-radiolabelled insert from pSPR13 (B). The linear plasmids from strains Sh-2-82 and ECM-NY-86 are not shown in this figure but these DNAs also failed to hybridize with insert from pSPR9 and pSPR13. The passaged variant of strain B31 that was used in this study does not carry SC plasmids. Arrows denote the SC plasmids that exhibited relatively weak or no hybridization signal. Linear molecular weight markers are indicated on the left and some of the SC plasmid sizes, determined by contour length measurements using pBR322 as an internal standard (data not shown), are indicated on the right.
Figure 3B:
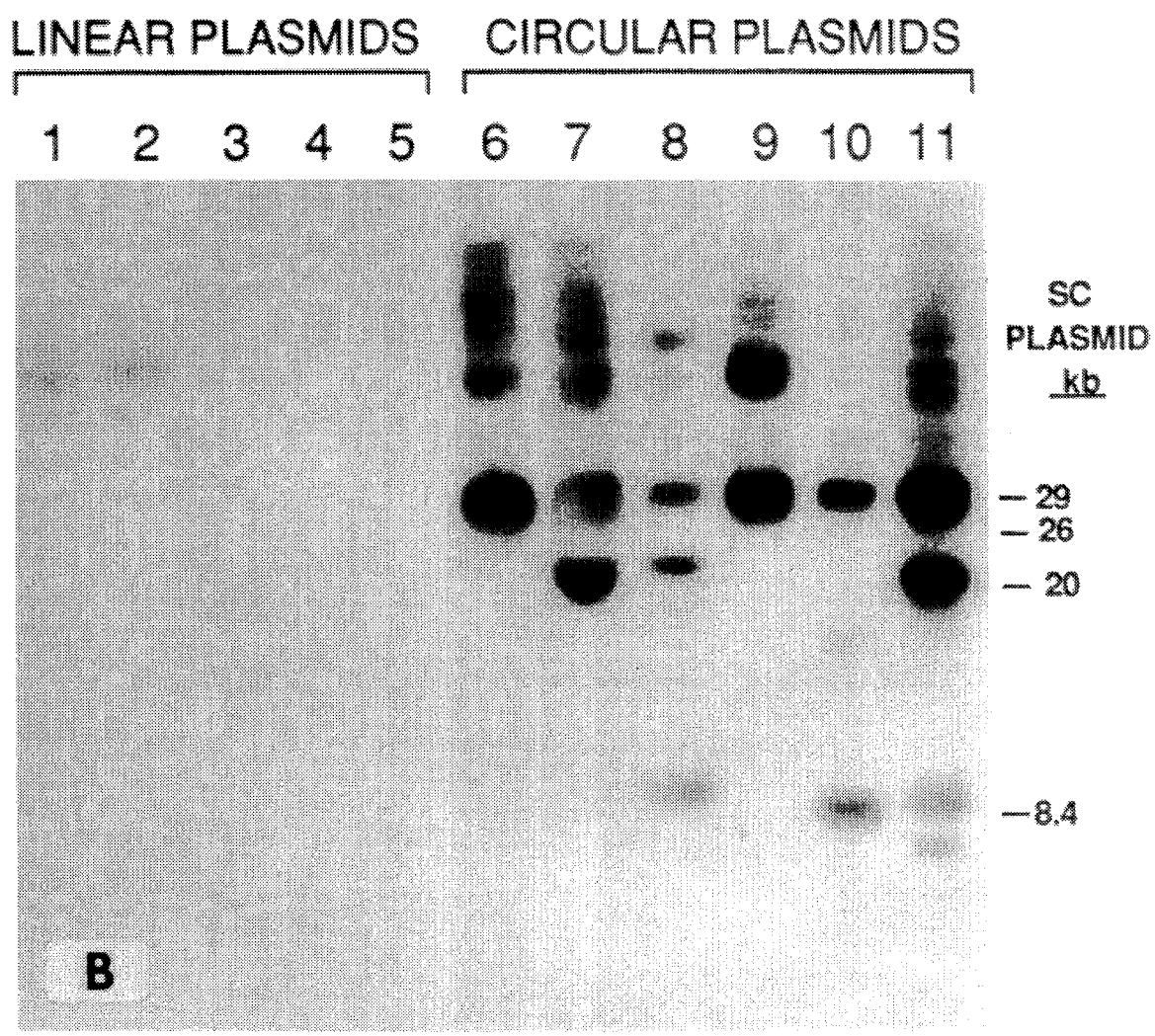
Figure 4:
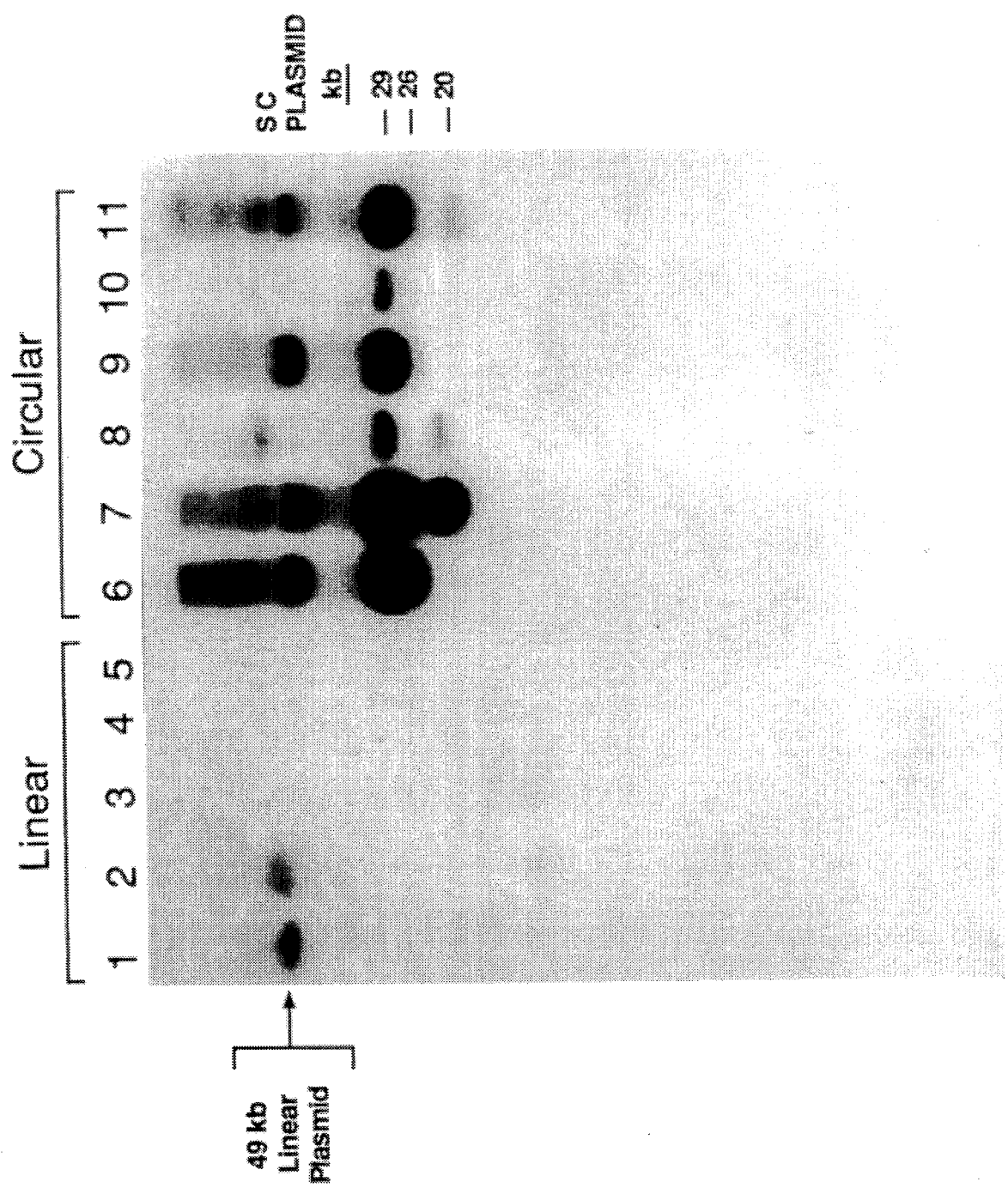
FIG. 4 is an autoradiograph showing hybridization of linear and SC plasmids from *B. burgdorferi* isolates with $^{32}$P-radiolabelled insert from pSPR9. The Southern blot described in FIG. 3 was stripped of the pSPR13 probe and rehybridized with insert from PSPR9.

The data indicates that spirochete DNA carried by pSPR9, pSPR13, and pSPR14 are from SC plasmids. Therefore, the extent to which these sequences are distributed among unrelated isolates was determined and it was also determined whether they are universally restricted to SC plasmids. Undigested SC and linear plasmid fractions from seven *B. Burgdorferi* isolates were examined by agarose-gel electro-phoresis (FIG. 3A) and then Southern blotted and probed with pSPR13 (FIG. 3B), pSPR14 (data not shown) and pSPR9 (FIG. 4). With the exception of strain B31, each strain carried a minimum of two SC plasmids and numerous linear plasmids, indicating that both forms were present in these studies. pSPR13 and pSPR14 both hybridized with the same DNA bands which included all detected SC plasmids except the 20 kb SC plasmid from strain CT20004.

pSPR9 hybridized with most of the SC plasmids, but differed from the other two clones in that it did not hybridize with the 8.4 and 8.8 kb SC plasmids, and it's hybridizing signal associated with the 20 kb plasmid carried by strain Sh-2-82 was relatively weak. This suggests that pSPR9 has less sequence similarity with the 20 kb plasmid from. strain Sh-2-82 than do pSPR13 and pSPR14. pSPR9 did not hybridize with the 29 kb SC plasmid from strain CT20004, indicating this plasmid is unique among all other SC plasmids identified in that it lacks both types of repeated DNA sequences. Chromosomal DNA from all isolates was assumed to be the smeared band in agarose-gels that comprised hererogenous fragmented DNA (data not shown) that migrated slightly slower than the 49 kb linear plasmid. pSPR9, pSPR13 and pSPR14 did not hybridize to this DNA, indicating that the sequences represented by these clones are not associated with chromosomal DNA.

All three clones hybridized with the 49 kb linear plasmid from strain B31 and a similar sized linear plasmid from strain CT26816. They did not hybridize with any other linear plasmids including the 49 kb linear plasmids carried by five other strains (FIG. 3). This indicates that the two types of repeated DNA sequences represented by pSPR13/pSPR14 and pSPR9 are only rarely found on linear plasmids, and when they are detected, they appear to be restricted to one size class.

Species-specificity of repeated DNA

Figure 5A:
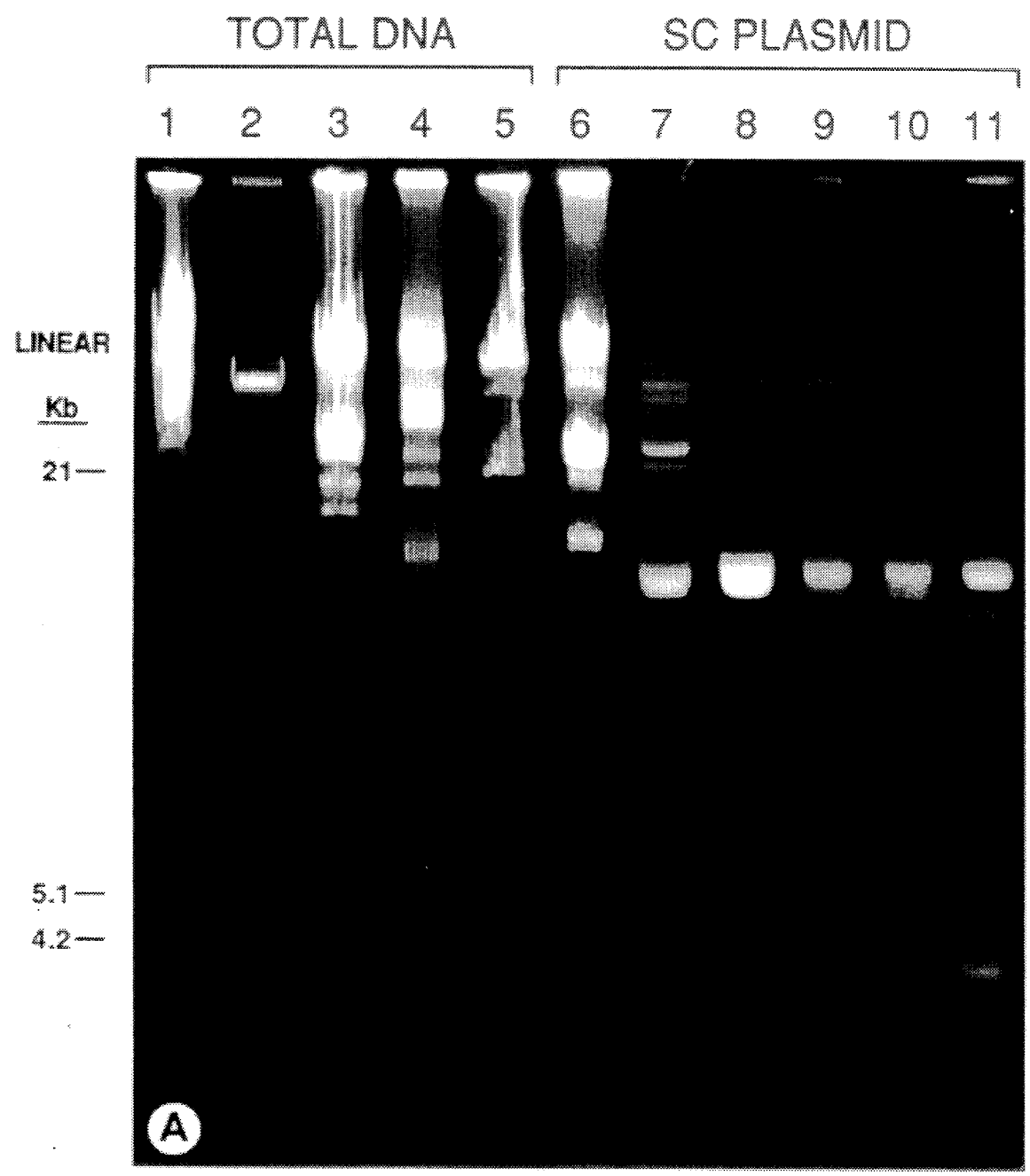
FIG. 5 is an autoradiograph showing hybridization of purified SC plasmids and total DNA from six Borrelia species with $^{32}$P-radiolabelled insert from pSPR13.
Figure 5B:
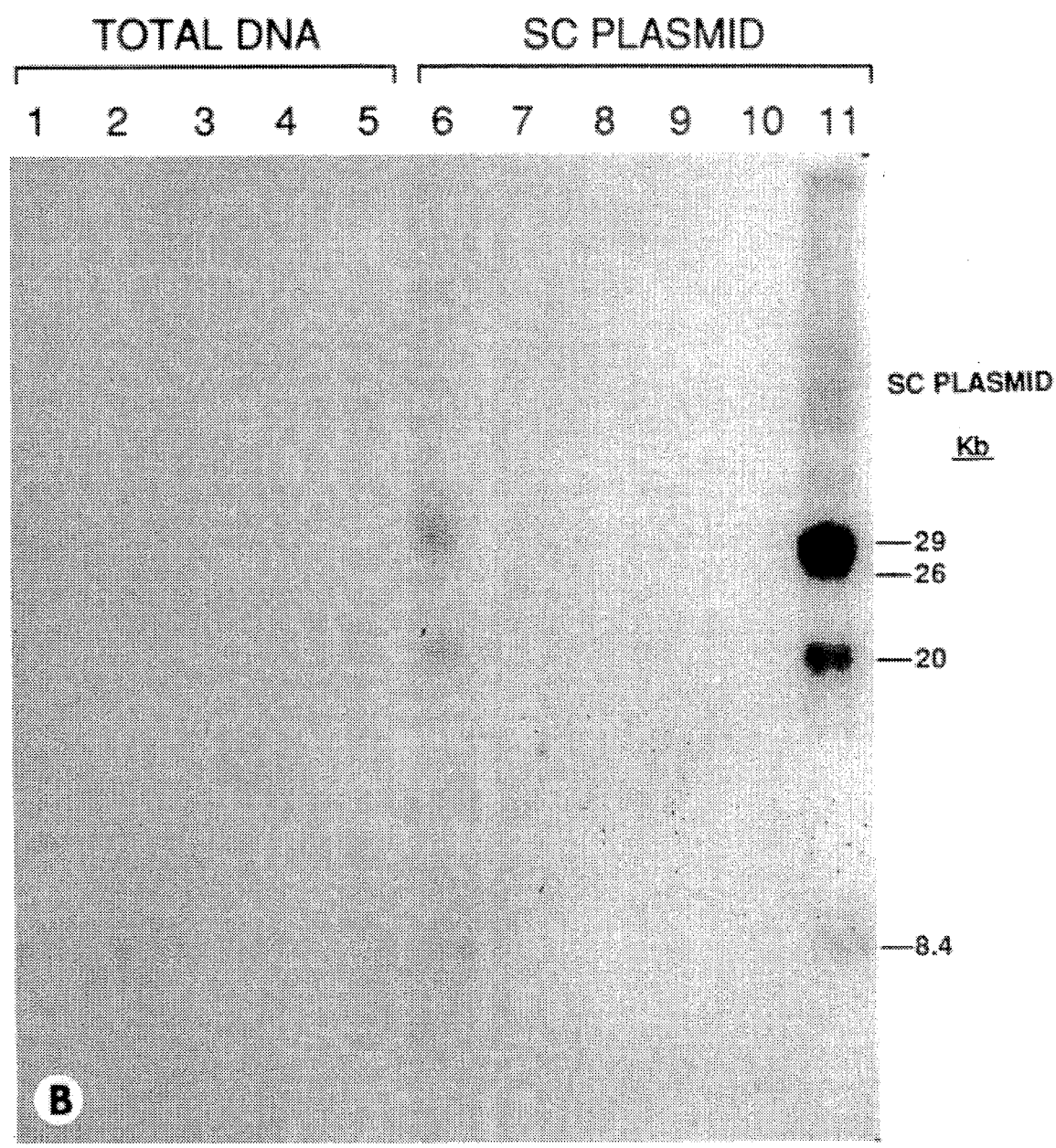

Repeated DNA sequences that have been described in bacteria are often species-specific. To determine if the plasmid sequences described here are also species-specific, DNA from five additional Borrelia species were probed with pSPR9 (data not shown) and pSPR13 (FIG. 5). These included two isolates of *B. hermsii* and one isolate of *B. turicatae, B. coriaceae, B. parkeri* and *B. anserina*. SC plasmid fractions were prepared for each species of Borrelia by ethidium bromide density-gradient centrifugation. Only the two *B. hermsii* isolates and the *B. coriaceae* and *B. turicatae* isolates, however, had a sufficient quantity of SC plasmid DNA in their bacterial lysates to retrieve by density-gradient centrifugation. None of the SC plasmids from these four strains or total DNA from the five Borrelia species hybridized with pSPR13 (FIG. 5) or pSPR9 (data not shown). This indicates that repeated DNA sequences represented by pSPR9 and pSPR13 are specific for *B. burgdorferi*.

Heteroduplex mapping of pSPR13 and pSPR14 sequence similarity

Figure 6A:
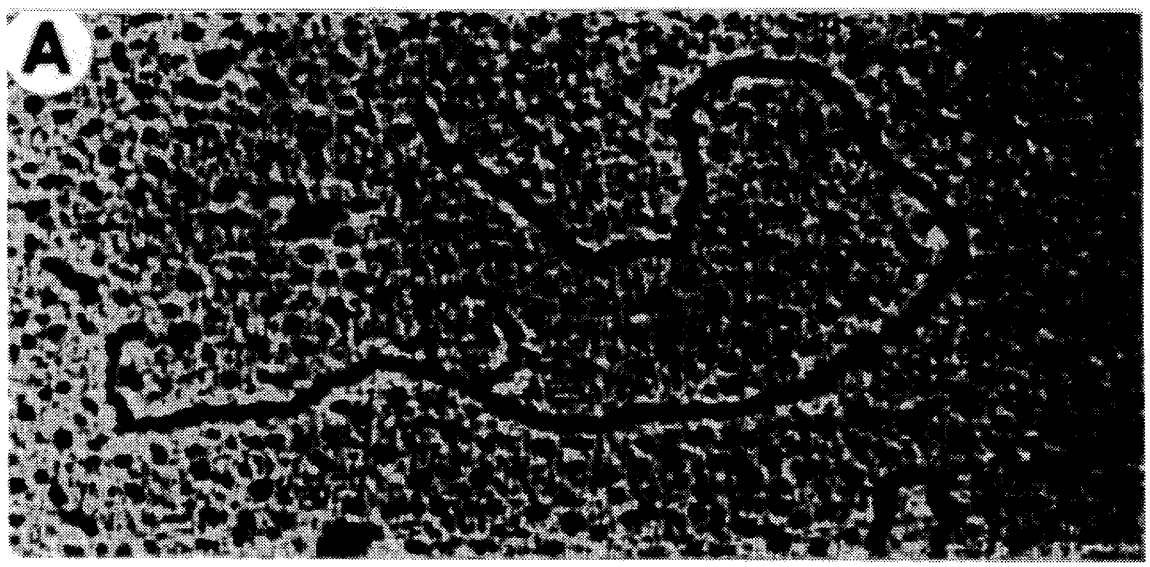
FIG. 6 shows electron micrographs of pSPR13 and pSPR14 heteroduplexes prepared under stringencies that permitted 25% (A) and 16% (B) basepair mismatch. (A) The length of the two strands which form the loop were 0.21+/−0.05 kb (pSPR14 DNA strand) and 0.78+/−0.10 kb (pSPR 13 DNA strand). This heterology was 1.40+/−0.14 kb from the closest end of the duplex. The lengths represent the average obtained from measuring 20 heteroduplex molecules (+/−standard deviation). (B) Insert is a schematic representation of the heteroduplex shown In panel B. Molecular lengths of each region were: (a) 1.39+/−0.14 kb; (b) 1.14+/−0.15 kb (pSPR13 DNA strand) and 0.49+/−0.08 kb (pSPR14 DNA strand); (c) 1.81+/−0.10 kb; (d) 1.54+/−0.25 kb; (e) 1.07+/−0.11 kb. The lengths represent the average obtained from measuring 11 heteroduplex molecules (+/−standard deviation). The arrow denotes the area defined by region "d" (insert) where the two strands are only partially homologous.
Figure 6B:
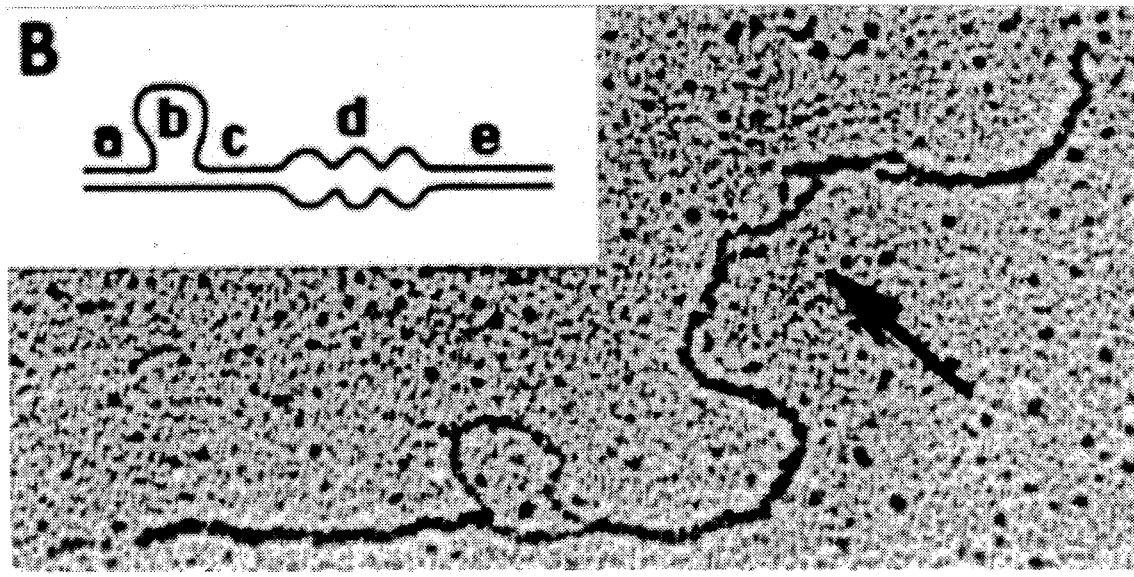

The signal detected for each SC plasmid probed with the cloned DNAs was variable, with the weakest signals associated with the 26 kb size class (FIG. 3, arrows). Although signal variability may in part be due to differences in plasmid concentration and/or the copy number of each sequence per plasmid, it may also be due to variation in the degree of sequence similarity between the probe and the various plasmid DNAs. Some, if not all, of the repeated DNAs may therefore reflect closely related but distinct sequences rather than a single sequence repeated many times. To examine this possibility, pSPR18 and pSPR14 sequences were compared by heteroduplex mapping. This technique can detect sequence variability along the length of DNA molecules shown to hybridize under high stringent conditions by Southern blot procedures.

pSPR13 and pSPR14 were linearized by AvaII digestion. This resulted in a 0.2 kb vector fragment and a double stranded molecule consisting of the cloned insert flanked by two vector DNA segments with molecular lengths of 1.0 kb and 1.4 kb. Following denaturation, the single strands were renatured and mounted for microscopy at two different, but relatively high, stringencies. At the lowest of the two stringencies, heteroduplexes contained only a single visible region of heterology (FIG. 6A). A 0.8 kb loop was measured 1.4 kb from the end of the duplex molecule. Heteroduplex molecules mounted at higher stringency (FIG. 6B) showed an apparent increase (0.3 kb) in the size of the loop while the length from the loop to the end of the duplex remained 1.4 kb. AT rich areas are known to melt at high stringency, particularly in the area where a homologous region adjoins a region of sequence mismatch, such as region "b". In view of this, and the fact that the length of the 0.3 kb section that melted is within the standard deviation obtained for region "b" at both stringencies, it cannot be concluded that this area represents a region of partial sequence mismatch. In addition to the loop observed at the higher stringency, however, a region of partial sequence mismatch (arrow) was observed and is labeled region "d" in the schematic insert. Spanning a region of approximately 1.5 kb, this area is characteristic of partial homology caused by the accumulation of genetic drift.

Homoduplexes showed no detectable structure at either stringency level ruling out strand denaturation at AT rich areas. The area of partial sequence mismatch (region "d") also served to orient the molecule with respect to vector and insert. Contour length measurements confirm that region "a" (schematic insert) must represent the longer (1.4 kb) of the two vector arms. Region "e" therefore represents the 1.0 kb vector segment. Region "c" (FIG. 6B) corresponds to 1.8 kb of highly similar sequences present in each strand. Since this portion of the duplex did not melt at the highest stringency. These data demonstrate that spirochete fragments carried by pSPR13 and pSPR14 share a highly conserved region of DNA, 1.8 kb in length, which is adjacent to a more variable region, 1.5 kb in length.

In summary, the data presented herein clearly show that *B. burgdorferi* isolated from a wide variety of geographical and biological sources carry multiple DNA sequences that have a high degree of sequence similarity and were only detected on plasmids. In addition, these DNA sequences appear to be species-specific, in that cloned fragments did not hybridize with DNA from any of the five additional Borrelia species tested. This included the most closely related spirochete, *B. hermsii*. The results indicate that the presence of repeated DNA sequences in *B. burgdorferi* serve as an amplified target for a diagnostic DNA probe, particularly since they are associated with SC plasmids which are indicated to be present in multiple copies. Furthermore, as these DNA sequences are found at multiple locations within each strain, by virtue of their association with several different plasmids, the continued identification of *B. burgdorferi* is assured despite the potential for the loss of DNA sequences during *in vitro* cultivation. For this reason, the use of such sequences as DNA probes has a considerable advantage over the use of other DNA sequences that are species-specific, but which are present in only one copy, or if present in multiple copies, restricted to a single location. Although some SC plasmids are relatively unstable during *in vitro* cultivation (Schwan et al, supra), in accordance with the present invention, the retention of most of the SC plasmids carried by strain Sh-2-82 for over two hundred *in vitro* passages have been observed indicating that most SC plasmids have sufficient stability to be useful targets for DNA probes used for species identification.

The wide distribution of SC plasmids carrying the repeated DNA sequences among *B. burgdorferi* assures the reliability of the diagnostic test of the present invention.

It has been found that the ability of the bacteria to cause disease may depend on genes which reside on extra-chromosomal elements such as SC plasmids (Elwell et al, 1980, *Annu. Rev. Microbiol.* 34:465–496). The loss of a 7.6 kb SC plasmid from *B. burgdorferi* during *in vitro* cultivation correlated with loss of infectivity for the white-footed mouse, *Peromyscus leucopus,* one of the natural reservoirs for *B. burgdorferi* (Schwan et al, supra). This further evidences the importance and reliability of detecting SC plasmid by the probes of the present invention.

Plasmids pSPR9, pSRP13 and pSPR14 have been deposited with the American Type Culture Collection (Rockville, Md.). These plasmids have been given accession numbers ATCC 69785, ATCC 69786 and ATCC 69787 respectively.

It is understood that the examples and embodiments described herein are for illustrative purposes only and that various modifications or changes in light thereof will be suggested to persons skilled in the art and are to be included within the spirit and purview of this application and scope of the appended claims.

Figure 1B:
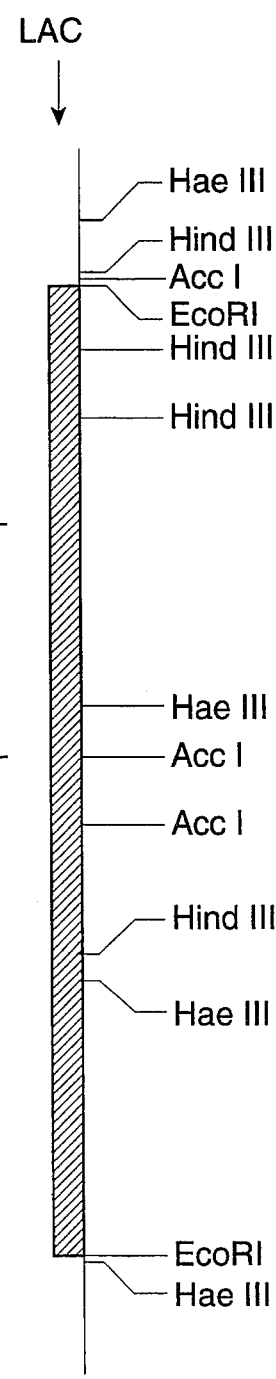
Figure 1C:
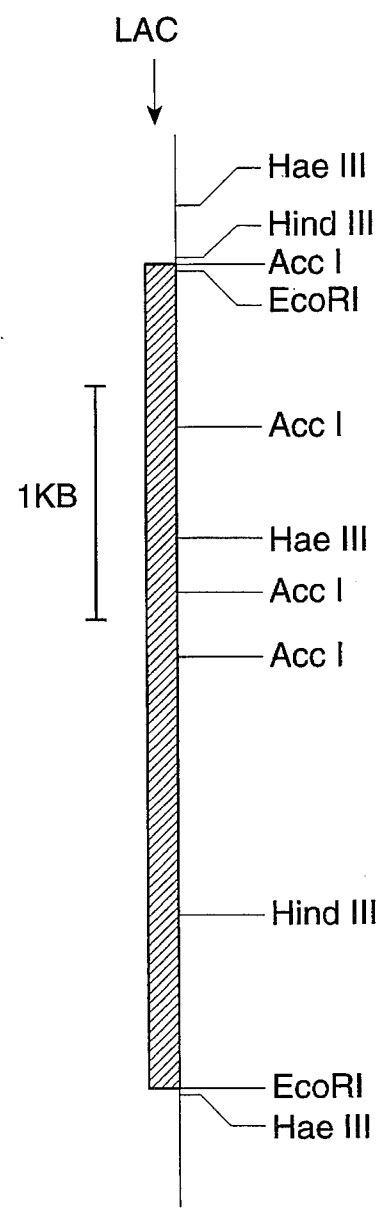

What is claimed is:

1. A nucleic acid probe specific for *Borrelia burgdorferi* DNA and not reactive with other Borrelia DNAs wherein said probe consists of pSPR14, pSPR13 and pSPR9 as shown in FIG. 1 and hybridizes with the repeated DNA sequence contained in *Borrelia burgdorferi* supercoiled circular plasmids which are present in multiple copies and in *Borrelia burgdorferi* linear plasmids.

2. A method for detecting infraction by *Borrellia burgdorferi*, comprising obtaining a body sample from a host suspected of having been infected by *Borrelia burgdorferi* and hybridizing the DNA obtained from said sample with the nucleic acid probe of claim 1, the occurrence of positive hybridization being indicative of the presence of *Borrelia burgdorferi*-infection in the host from which said sample was obtained.

3. A diagnostic kit for the detection of *Borrelia burgdorferi* DNA, comprising a container containing the nucleic acid probes of claim 1.

* * * * *